(12) United States Patent
Szabó et al.

(10) Patent No.: US 11,565,062 B2
(45) Date of Patent: Jan. 31, 2023

(54) APPARATUS FOR CATALYTIC DECOMPOSITION OF NITROUS OXIDE IN A GAS STREAM

(71) Applicant: Medclair AB, Stockholm (SE)

(72) Inventors: István Szabó, Boda Kyrkby (SE); Jerker Sundling, Borlänge (SE); Tomas Nyberg, Uppsala (SE)

(73) Assignee: Medclair AB, Stockholm (SE)

( * ) Notice: Subject to any disclaimer, the term of this patent is extended or adjusted under 35 U.S.C. 154(b) by 650 days.

(21) Appl. No.: 16/606,102

(22) PCT Filed: Apr. 19, 2018

(86) PCT No.: PCT/EP2018/060063
§ 371 (c)(1),
(2) Date: Oct. 17, 2019

(87) PCT Pub. No.: WO2018/193043
PCT Pub. Date: Oct. 25, 2018

(65) Prior Publication Data
US 2021/0146075 A1 May 20, 2021

(30) Foreign Application Priority Data
Apr. 21, 2017 (SE) .................................... 1750475-4

(51) Int. Cl.
*B01D 53/02* (2006.01)
*A61M 16/00* (2006.01)
(Continued)

(52) U.S. Cl.
CPC ..... *A61M 16/0093* (2014.02); *B01D 53/0438* (2013.01); *B01D 53/8631* (2013.01);
(Continued)

(58) Field of Classification Search
CPC ...... A61M 16/0093; A61M 2202/0283; B01D 2253/102; B01D 2253/306;
(Continued)

(56) References Cited

U.S. PATENT DOCUMENTS 7,235,222 B2  6/2007  Hotta et al.
7,597,858 B2  10/2009  Hotta et al.
(Continued)

FOREIGN PATENT DOCUMENTS

DE  43 08 940 A1  9/1994
EP  2 165 756 B1  10/2012
(Continued)

*Primary Examiner* — Christopher P Jones
(74) *Attorney, Agent, or Firm* — Blank Rome LLP

(57) ABSTRACT

The invention relates to an apparatus (1) for catalytic decomposition of nitrous oxide in a gas stream derived from exhalation air from a patient. The apparatus (1) comprises an inlet arrangement (2) with a gas inlet (3) for the exhalation air, an outlet arrangement (11) with a gas outlet (12) for an outlet gas, and between these arrangements a through-flow decomposition chamber (9) containing a catalyst material. According to the invention the apparatus is provided with a nitrous oxide adsorption/desorption means (4) in the inlet arrangement (2) for level out variations in the concentration of nitrous oxide fed to the decomposition chamber (9).

5 Claims, 4 Drawing Sheets

(51) Int. Cl.
*B01D 53/04* (2006.01)
*B01D 53/86* (2006.01)
*B01J 20/18* (2006.01)
*B01J 20/20* (2006.01)
*B01J 20/28* (2006.01)

(52) U.S. Cl.
CPC .......... *B01D 53/8696* (2013.01); *B01J 20/18* (2013.01); *B01J 20/20* (2013.01); *B01J 20/28064* (2013.01); *B01J 20/28066* (2013.01); *A61M 2202/0283* (2013.01); *B01D 2253/102* (2013.01); *B01D 2253/306* (2013.01); *B01D 2255/1023* (2013.01); *B01D 2257/402* (2013.01); *B01D 2259/40088* (2013.01); *B01D 2259/455* (2013.01); *B01D 2259/4533* (2013.01)

(58) Field of Classification Search
CPC ...... B01D 2255/1023; B01D 2257/402; B01D 2259/40088; B01D 2259/4533; B01D 2259/455; B01D 53/04; B01D 53/0438; B01D 53/8631; B01D 53/869; B01D 53/8696; B01J 20/18; B01J 20/20; B01J 20/28064; B01J 20/28066; Y02C 20/10
See application file for complete search history.

(56) References Cited

U.S. PATENT DOCUMENTS

| | | |
|---|---|---|
| 2003/0185735 A1 | 10/2003 | Hotta et al. |
| 2005/0281724 A1 | 12/2005 | Hotta et al. |
| 2011/0262332 A1* | 10/2011 | Szabo ............... A61M 16/0093 422/120 |
| 2012/0087851 A1* | 4/2012 | Deuerlein ............... C07C 51/42 423/239.2 |
| 2014/0017139 A1* | 1/2014 | Szabo .................... B01D 53/04 422/173 |
| 2014/0020685 A1* | 1/2014 | Szabo .................... B01D 53/04 128/203.29 |
| 2015/0246197 A1* | 9/2015 | Sundling ............... A61M 16/20 128/202.22 |
| 2016/0082382 A1 | 3/2016 | Doong et al. |
| 2022/0106897 A1* | 4/2022 | Garbujo ................. B01J 23/745 |

FOREIGN PATENT DOCUMENTS

| | | |
|---|---|---|
| JP | 2000-093740 A | 4/2000 |
| JP | 2010-005584 A | 1/2010 |
| WO | WO 02/26355 A2 | 4/2002 |
| WO | WO 2012/128694 A1 | 9/2012 |

* cited by examiner

US 11,565,062 B2

APPARATUS FOR CATALYTIC DECOMPOSITION OF NITROUS OXIDE IN A GAS STREAM

FIELD OF THE INVENTION

The present invention relates to an apparatus for catalytic decomposition of nitrous oxide in a gas stream derived from exhalation air from a patient according to the preamble of claim 1.

BACKGROUND OF THE INVENTION

Mixtures of nitrous oxide ($N_2O$) and oxygen ($O_2$) are widely used in medicine for pain relief.

Within health care units, nitrous oxide is used within surgery, dental care, maternity care during delivery etc. due to its anaesthetic and analgesic effects on patients. The typical patient is allowed to inhale a gas mixture (inhalation air) in which the main components are nitrous oxide, typically in concentrations ≥10%, such as ≥20% and/or ≤80%, such as ≤70% (v/v) and oxygen.

The composition of the air exhaled by a patient receiving nitrous oxide is essentially the same as the composition of the inhaled air except that there typically are increases in moisture content (water) and carbon dioxide. Exhaled air from patients inhaling nitrous oxide is typically handled in a waste gas handling system which is common for several rooms/patients. In this kind of system, the exhaled air is typically diluted with ambient air (e.g. 2-50 times), and the exhaled air is finally treated at the health care unit, e.g. in an apparatus for removal of nitrous oxide and/or is passed into the environment.

In cases when a waste gas handling system is not used exhaled residual nitrous oxide has usually been released into the room/surroundings in which the patient is treated which means that also personnel such as doctors, dentists, nurses, for instance, is exposed to nitrous oxide, or directly into the environment via an exhaust system. Nitrous oxide exposition over a long period of time, however, can be harmful to such personnel even at very low concentrations in case of frequent exposition over many years. Occupational health limits have been set to 15-25 ppm.

Furthermore, nitrous oxide is an air pollutant which is considered at least 300 times more effective than carbon dioxide as a "greenhouse gas".

Nitrous oxide as such spontaneously decomposes when heated to temperatures of about 600° C. or higher into nitrogen and oxygen in a molar ratio of 2:1 with significant amounts of undesired by-products such as nitrogen oxides other than nitrous oxide, e.g. $NO_x$ (where x is 1 or 2). The reaction is strongly exothermic, and at concentrations of nitrous oxide higher than about 1-2% problems may occur. Also, the reaction rate increases with increasing temperature. This means that once the reaction is started, strict temperature control will be required if the reaction is to be used for the removal/decomposition of nitrous oxide in waste gases containing elevated concentrations of nitrous oxide. Specific precautions are needed in order to control the amounts of $NO_x$ since discharge of $NO_x$ to the environment is strictly regulated.

It is known that by using catalysts promoting decomposition of nitrous oxide an acceptable decomposition can be accomplished at lower concentrations of nitrous oxide (below 1-2%) and at temperatures significantly below 600° C.

With proper selection of catalysts acceptable levels of undesired by-products, such as $NO_x$, can easily be accomplished. Should the nitrous oxide to be dealt with have a high concentration this implies problems with its destruction at a health care unit.

During treatments involving administration of nitrous oxide, the patient is periodically inhaling air containing nitrous oxide, and the frequency of inhaling depends upon the desired pain relief. Exhalation air will thus contain very high concentrations of nitrous oxide interrupted with irregular periods of zero concentration of nitrous oxide. This means that precautions are required when decomposing nitrous oxide in exhaled air from a single patient (close to the patient), particularly when using a mobile nitrous oxide catalytic decomposition unit. During periods of high concentrations, the catalytic decomposition unit has increased risks of a) overheating and explosion due to an uncontrolled acceleration of the temperature, and b) formation of undesired levels of harmful by-products, such as $NO_x$. The irregular switches between high and zero concentration of nitrous oxide further complicate the situation since this will mean uncontrolled switches in outcome of the reaction (products/by-products), reaction rate, concentrations, temperature etc.

There is a demand for a mobile apparatus for decomposition of nitrous oxide derived from exhalation air containing nitrous oxide where the decomposition is carried out
a) at exothermic conditions, and/or
b) close to the patient, i.e. with the patient directly connected to the apparatus for decomposition of nitrous oxide.

An important demand on the apparatus is that the processed gas discharged from the apparatus must have an acceptable composition and temperature for being delivered into the room in which the patient and/or other people are present and/or the apparatus is placed.

The apparatus should therefore be able to provide sufficiently high reduction levels of nitrous oxide and formation of sufficiently low levels of nitrogen oxides, such as $NO_x$.

Other demands include that the flow velocity, amount, temperature etc. of the discharged gas shall be acceptable for the ventilation of the room in which the patient and/or personnel and/or the apparatus are present. Still other demands relate to effective control of the exothermic self-sustaining decomposition reaction that occurs at higher concentrations of nitrous oxide.

A further demand relates to heating the decomposition reactor when no nitrous oxide is feed to the decomposition reaction, i.e. during stand-by phases of the apparatus for decomposition of nitrous oxide when the patient is not exhaling air containing nitrous oxide, since the reactor must have a certain minimum temperature to be able to decompose the nitrous oxide properly.

EP 2 165 756 B1 relates to a method for decomposition of nitrous oxide in a gas stream. In said document the problem of maintaining a certain minimum temperature of the decomposition reactor during stand-by phases of the apparatus for decomposition of nitrous is described, i.e. during periods when the patient is receiving pain relief but not exhaling air containing nitrous oxide. This problem is solved according to said document by during stand-by phases passing heated gas substantially free of nitrous oxide through the nitrous oxide decomposition reactor so as to maintain the necessary decomposition temperature of the decomposition reactor.

A further problem with catalytic decomposition of nitrous oxide is that, in case high concentrations of nitrous oxide is feed to the decomposition reactor, the temperature of the decomposition reactor may be too high which may destroy the catalyst of the decomposition reactor. In practice, this may have significant implications at levels of nitrous oxide exceeding concentrations of 15 000 to 20 000 ppm. In particular, this applies at very high concentrations of nitrous oxide in excess of 50 000 to 200 000 ppm. At these concentrations, local hot spots (local high temperature rise) can occur in the catalyst which can be destructive.

A solution to this problem is also disclosed in EP 2 165 756 B1. The device for catalytic decomposition of nitrous oxide according to said document may comprise a mixing means upstream of the nitrous oxide decomposition reactor for mixing the incoming gas with a diluting gas, preferably with ambient air, wherein the quantity of the diluting gas can be controlled between 0% and 100% so as to reduce the concentration of the nitrous oxide fed to the reactor.

Said document also discloses the possibility to buffer the nitrous oxide containing gas exhaled by a patient e.g. in a rigid or elastic gas chamber, a hydraulic chamber or in a pressure tank by which it is possible to reduce peaks or fluctuations in the flow rate, e.g. caused by breathing of the patient and thus to smoothen the flow-rate of nitrous oxide containing gas further processed in the decomposition device.

OBJECT OF THE INVENTION

Thus, an object of the invention is to provide an apparatus for carrying out catalytic decomposition of nitrous oxide used in health care to $N_2$ and $O_2$, i.e. which derives from exhalation air from one or more patient(s) receiving pain relief by inhaling oxygen containing nitrous oxide, by which the concentration of nitrous oxide passed to the decomposition reactor is leveled out in that only the nitrous oxide part of the exhalation air is stored so as to on the one hand avoid the necessity to during stand-by phases pass heated gas substantially free of nitrous oxide through the nitrous oxide decomposition reactor for heating the same to the reaction temperature necessary and on the other hand to avoid the necessity to mix the incoming gas with a diluting gas or by any other means such as buffering, for instance, so as to reduce the concentration of nitrous oxide passed to decomposition reactor to avoid overheating/hot spots and destruction of the same.

A further object of the invention is to provide an apparatus for carrying out catalytic decomposition of nitrous oxide which is mobile and thus be used close to a patient receiving pain relief by inhaling oxygen containing nitrous oxide.

BRIEF DESCRIPTION OF DRAWINGS

The invention will now be described by way of a non-limiting example with reference to the accompanying drawing, in which.

DESCRIPTION OF PREFERRED EMBODIMENTS

Figure 1:
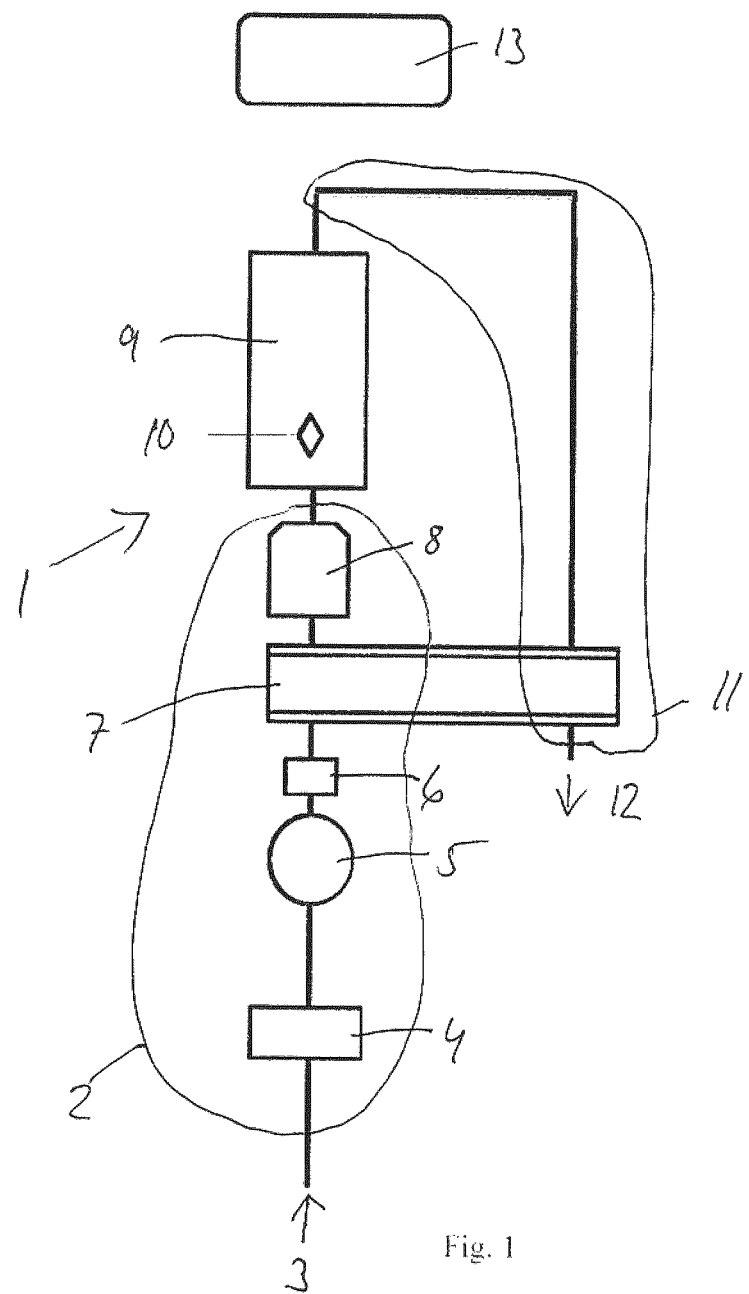
FIG. 1 is a schematic view of an apparatus for catalytic decomposition of exhaled nitrous oxide having an inlet arrangement provided with a nitrous oxide adsorption/desorption means according to the invention.

FIG. 1 show a schematic view of an apparatus 1 for catalytic decomposition of nitrous oxide contained in a gas mixture exhaled by a patient, the apparatus 1 preferably being in the form of a mobile unit to be used close to at least one patient receiving pain relief.

Said apparatus 1 comprises, as seen in the flow direction of the gas mixture to be treated, an inlet arrangement 2 comprising a gas inlet 3 for an inlet gas being a mixture of oxygen containing gas and nitrous oxide, at least one adsorption/desorption means 4 for selective adsorption/desorption of nitrous oxide, a fan 5, a flow meter 6, a heat exchanger 7, and a heater 8. The apparatus 1 further comprises a nitrous oxide decomposition reactor 9 provided with at least one temperature sensor 10, an outlet arrangement 11 comprising at least a gas outlet 12, and a control unit 13 for controlling and monitoring the temperature and gas flow in the nitrous oxide decomposition reactor and possibly for heating the adsorption/desorption means 4. The control unit 13 is connected (not shown) in a suitable way to the apparatus 1.

The apparatus 1 for decomposition of nitrous oxide may also comprise at least one gas analyzer, (not shown), preferably of IR type, for measuring the concentration of nitrous oxide feed to the nitrous oxide decomposition reactor 9.

The adsorption/desorption means 4 for selective adsorption/desorption of nitrous oxide is preferably in the form of at least one container 4 having gas inlet means and gas outlet means (not shown) and is filled with a suitable material that is able to adsorb/desorb preferably only nitrous oxide. In one embodiment, the container 4 is filled with activated carbon, preferably of the type bituminous coal based or coconut, having a surface area of about 500 to 2000 $m^2/g$. The container 4 may be filled with other material(s) or a mixture of materials suitable for adsorption/desorption of nitrous oxide, such as zeolite(s).

Since nitrous oxide has the property regarding the activated carbon that it is physically adsorbed (but not chemically) to the activated carbon/zeolite surface, this property is also reversible, i.e. the activated carbon easily release the nitrous oxide when the concentration in the gas mixture containing nitrous oxide is decreased. This means in practice that nitrous oxide is first adsorbed onto the activated carbon as long as the concentration is maintained and the activated carbon micro pores are available, i.e. they are not filled with nitrous oxide. This process is stopped when the activated carbon micro pores are filled. Furthermore, when the concentration of nitrous oxide decreases, the activated carbon will release the nitrous oxide into the environment and the concentration goes gradually down with respect to the nitrous oxide in the gas. Eventually the carbon will release all of its adsorbed nitrous oxide.

This means the activated carbon/zeolite is thus available to take up new nitrous oxide since the micro pores have been emptied.

Note further that the actual release procedure, i.e. the speed at which the nitrous oxide is released from the activated carbon micro pores and comes out in the gas phase again depends on the diffusion constant as well as the temperature of the activated carbon.

To increase the rate of desorption of nitrous oxide the container 4 or at least the activated carbon may be heated, if necessary.

Thus, the adsorption/desorption of the nitrous oxide of the inlet gas should be made in such a way that the concentration of the nitrous oxide in said gas to be treated after the adsorption/desorption means 4 should provide a self-sustaining decomposition reaction in the decomposition reactor 9. Thus, the concentration of nitrous oxide passed to the decomposition reactor 9 is leveled out since only the nitrous oxide part of the exhalation air is stored which means that during periods of time when the inlet gas is rich in nitrous oxide, the nitrous oxide will be stored in adsorption/desorption means 4, and when the inlet gas is lean in nitrous oxide, the nitrous oxide will be released from adsorption/desorption means 4. By this storage/release function of the adsorption/desorption means 4 it is possible to reduce/level out the concentration of nitrous oxide fed to the decomposition reactor 9 to avoid overheating/hot spots of the catalyst and destruction of the same. In the same way, since the nitrous oxide will be released/desorbed under quite some time when no or only a low concentration of nitrous oxide is present in the inlet gas it is not necessary to, during stand-by phases of the apparatus, pass heated gas substantially free of nitrous oxide through the nitrous oxide decomposition reactor for heating the same to the reaction temperature necessary.

Below, with reference to FIG. 2, a test apparatus 1 is described for determining the function and capacity of the adsorption/desorption means 4. In the test the adsorption/desorption means 4 in the form of a container 4 was filled with activated carbon of coconut type.

Equipment

Figure 2:
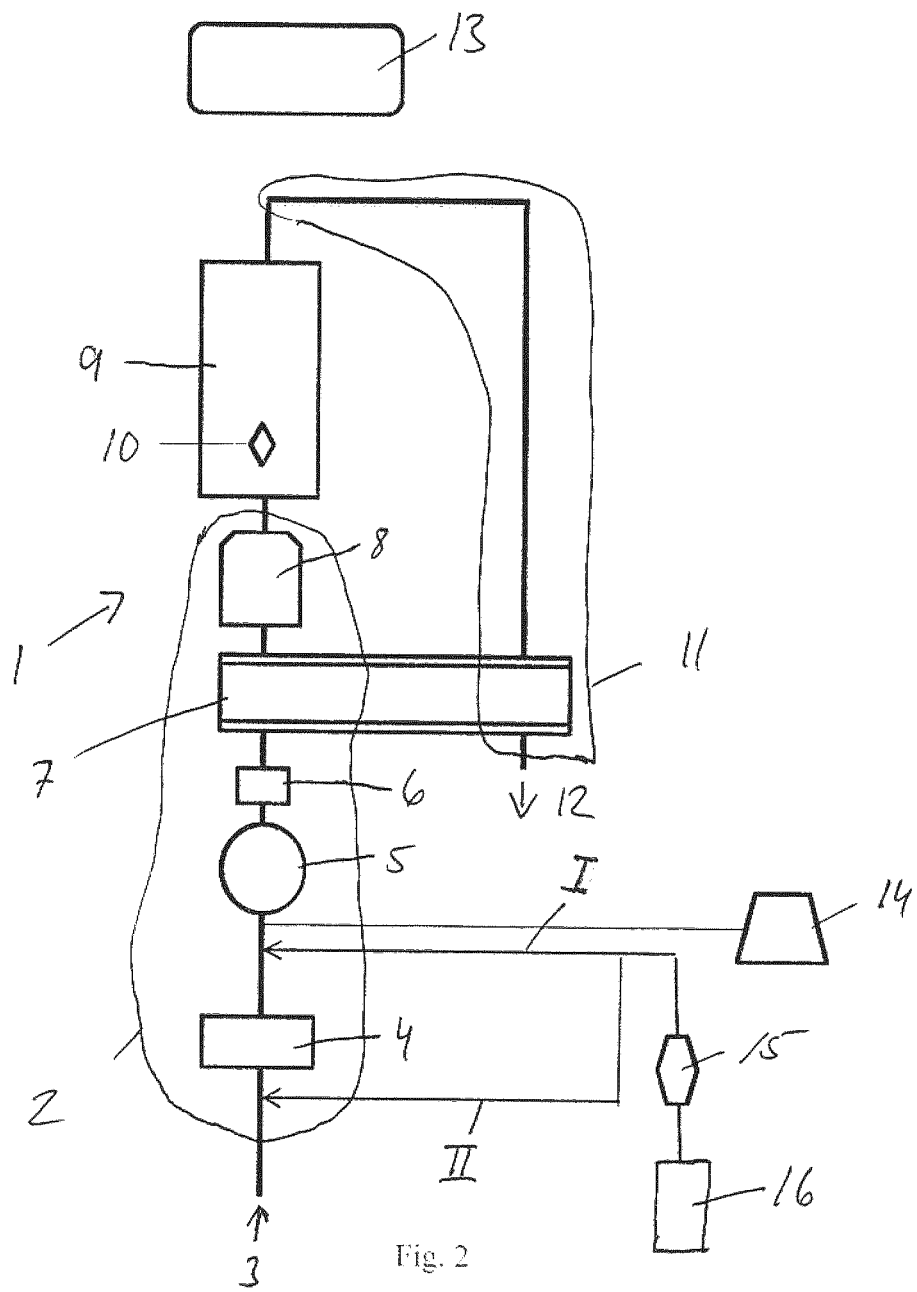
FIG. 2 is a schematic view of the apparatus shown in FIG. 1 arranged for testing of the nitrous oxide adsorption/desorption means according to the invention.

As seen in FIG. 2, the test apparatus 1 of essentially the same type as described above with reference to FIG. 1, was used. The test apparatus 1 was further provided with gas analyzer 14 for measuring the nitrous oxide concentration and of type IR having a measuring range of 0 to 100 000 ppm and a mass flow controller 15 for nitrous oxide for determining the amount of nitrous oxide fed into the test apparatus. The mass flow of nitrous oxide can be between 0.5-100 g/min.

The adsorption/desorption means 4 comprised activated carbon of coconut type, having a surface area of about 1200 to 1500 m$^2$/g. The activated carbon container could hold about 3 litres of activated carbon.

The flow meter 6 was provided for the control of gas flow in the test apparatus 1.

The temperature sensor 10 was provided in the catalyst bed and was of type thermocouple.

The catalyst was a catalyst for the decomposition of nitrous oxide into $N_2$ and $O_2$. The catalyst consisted of about 0.1-2% palladium on an aluminium carrier.

The catalyst bed could accommodate up to 2 litres catalyst material.

The fan 5 was speed-controlled and the gas flow may vary between 2-6 m$^3$/h.

Pure nitrous oxide from a gas bottle 16 was mixed with oxygen to simulate exhalation air coming from a patient in receipt of pain relief and fed to the inlet arrangement 2 of the test apparatus 1 either before the adsorption/desorption means 4 (line II) or after the adsorption/desorption means 4 (line I).

Experimental Data

Air gas flow: 2.6 Nm$^3$/h

Supplied amount of $N_2O$: 7 g/min

Reactor temperature 400-450° C.

Gas concentration $N_2O$: 85 000 ppm

Run time: 10-30 minutes

In the experiments below the adsorption/desorption means 4 for the nitrous oxide is called activated carbon means.

The experiments were designed to simulate real conditions in connection with the uptake of expiratory air from the patient during typical pain relieving procedures. In these cases, nitrous oxide was used for simulating pain relief of a patient. For example, in such a procedure, the patient normally inhales a gas mixture consisting of 50% nitrous oxide and 50% oxygen. A normal nitrous oxide consumption regarding this procedure is about 10-15 l/min of this gas mixture. This corresponds to about 10-15 grams of pure nitrous oxide per minute. Due to technical reasons, the maximum limit was set to 7 gram/min.

A normal treatment of a patient is about 15-30 minutes.

During the treatment, the patient normally receives nitrous oxide gas mixture for about 2-5 minutes via a breathing mask. After receiving the nitrous oxide gas mixture, the patient is breathing room air for about 1-2 minutes after which the patient again inhales nitrous oxide gas mixture through the mask. This whole process takes about 15-30 minutes depending on the extent of the procedure itself.

In this mask, the patient breathes in and out. Upon inhalation, the patient receives the nitrous oxide gas mixture and upon exhalation, the patient breathes out the nitrous oxide gas mixture. The exhalation air is sucked up in a hose connected to the mask and further transported by a fan to e.g. a mobile nitrous oxide destruction unit where the nitrous oxide gas is destructed.

It was found that during these conditions, the concentration of nitrous oxide in the inlet arrangement of the test apparatus 1 was about 50 000-150 000 ppm depending on the technical conditions.

The experiments disclosed herein were performed in order to stabilize the reactor temperature and minimize the risk of hot spots in the catalyst. This is accomplished by utilizing the properties of the activated carbon to adsorb nitrous oxide, i.e. to take up nitrous oxide for later release when the concentration of nitrous oxide is reduced in the gas stream.

From the conducted tests, it is concluded that the activated carbon can take up about 2 percent by weight of nitrous oxide, i.e. 1 kilo of activated carbon may adsorb about 20 grams of nitrous oxide.

Results

Below are the results of different experiments. Experiment 1 concerns injection of nitrous oxide gas after the activated carbon means. This means that the nitrous oxide gas does not pass through the activated carbon means. Experiment 2 concerns injection of nitrous oxide gas before the activated carbon means. In the latter case, the nitrous oxide gas is first taken up by the activated carbon means before being fed to the catalyst, i.e. the activated carbon means is acting as the adsorption/desorption means 4.

The experiments 1 and 2 show that the temperature of the catalyst increases with time. This is natural since this high level of nitrous oxide also generates heat which is detectable. Note that in these experiments, no additional supply of heat was added after the nitrous oxide was introduced into the reactor.

In FIG. 2 experiment 1 named "Without means" is shown by dotted line and experiment 2 named "With means" is shown by continuous line in which the nitrous oxide containing gas is fed via the activated carbon means.

The experiments 1 and 2 show that the activated carbon retains nitrous oxide long enough to hold the concentration of the gas down in the catalyst and thus hold the reactor temperature in the catalyst down. The difference between experiments 1 and 2 is about 60° C. under these conditions after 12 minutes.

Figure 3:
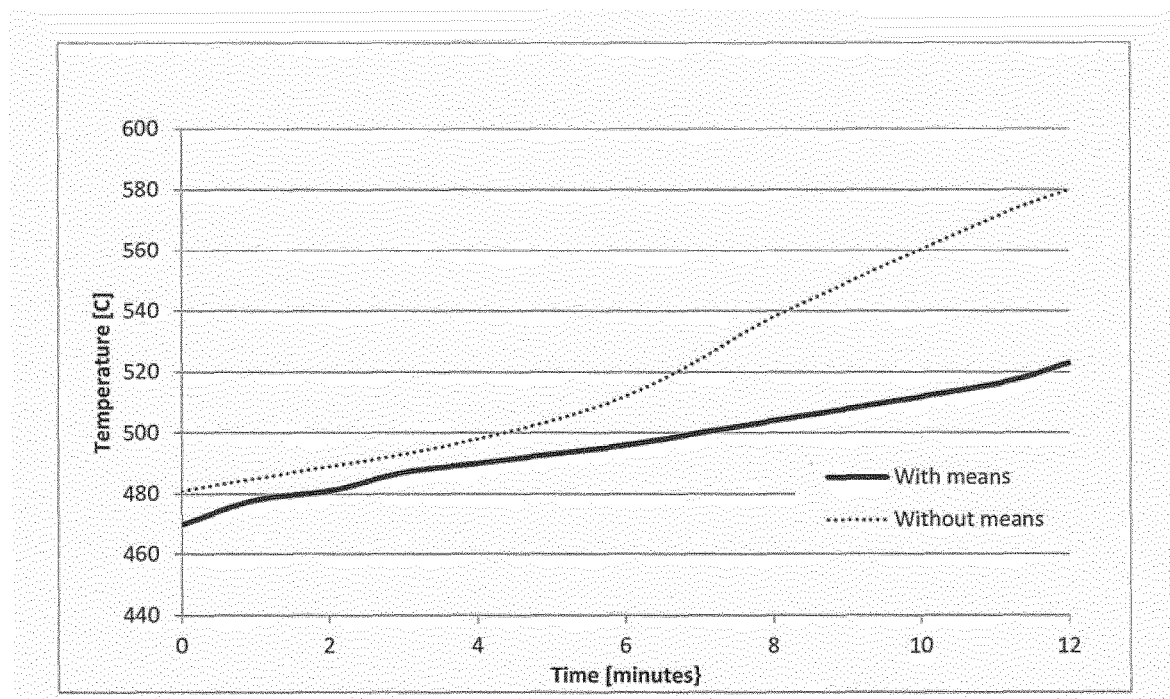
FIG. 3 is a diagram showing the temperature in the decomposition reactor with a nitrous oxide adsorption/desorption means (black line) and without a nitrous oxide adsorption/desorption means (dotted line)
Figure 4:
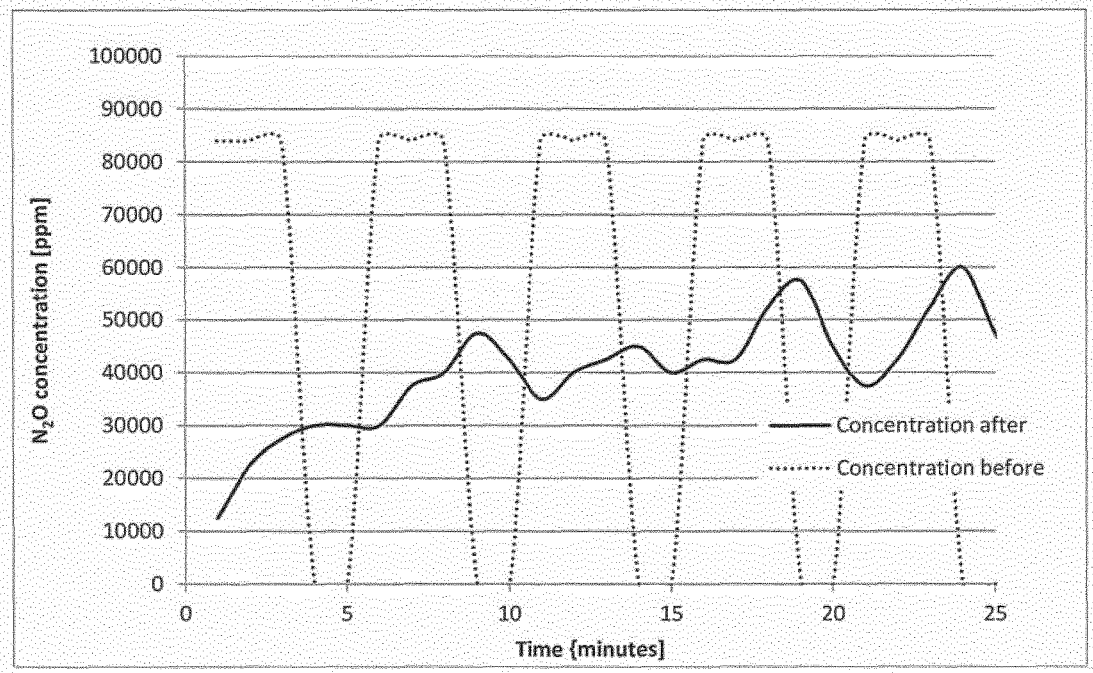
FIG. 4 is a diagram showing the fluctuation of nitrous oxide measured at the inlet of the catalytic reactor in case a concentration of 85 000 ppm of nitrous with stand-by phases with no nitrous oxide is passed to the inlet arrangement of the apparatus for decomposition of exhaled nitrous oxide, wherein the black line shows the concentration in case the inlet arrangement is provided with a nitrous oxide adsorption/desorption means according to the invention and the dotted line shows the concentration of nitrous oxide without the adsorption/desorption means according to the invention.

The experiment disclosed in FIG. 3 was conducted to see the activated carbon's ability to reduce and level out the concentration of nitrous oxide in a simulated case of a normal processing procedure for pain relief. The experiment was conducted by letting the incoming nitrous oxide first pass through the activated carbon means before entering the catalyst. Nitrous oxide was fed for about 3 minutes and then turned off for about 2 minutes. The air flow through the catalyst was kept constant at about 2.6 Nm$^3$/h all the time. Power supply to the heater was turned off after initial heating of the decomposition reactor to the necessary reaction temperature. The whole test lasted about 25 minutes.

The experiment shows that when the no activated carbon means is used the concentration of nitrous oxide fed to the catalyst is 85 000 ppm for 3 minutes and then down to zero. Thereafter, the level rises back to 85 000 ppm after a break of about 2 minutes.

When the activated carbon means is used the concentration of nitrous oxide is slowly rising in the catalytic reactor/apparatus.

Note that the nitrous oxide is supplied in the same way as above, i.e., alternately in the range of 3 min on and 2 min off.

When the activated carbon means is used, the level of nitrous oxide is kept at a comfortable level during the entire process time and the gas fed to the catalytic reactor is never free from nitrous oxide. The latter also means that the temperature of the catalytic reactor can be maintained and no additional supply of energy in the form of heated air substantially of nitrous oxide has to be fed to the reactor. The activated carbon means makes sure to maintain a high enough level of nitrous oxide throughout the treatment process to sustain an exothermic reaction.

Conclusions

Advantages of an activated carbon means are that the concentration of nitrous oxide rises slowly in the system and is significantly lower than without the activated carbon means. This gives a lower temperature rise in the reactor.

Overall, this eliminates the possibility of hot spots in the catalyst bed.

Malfunctions due to overheating have thereby significantly been reduced.

Another advantage is that the process is self-sustained with respect to energy since the level of nitrous oxide is smoothed out compared to without an activated carbon means.

Figure 5:
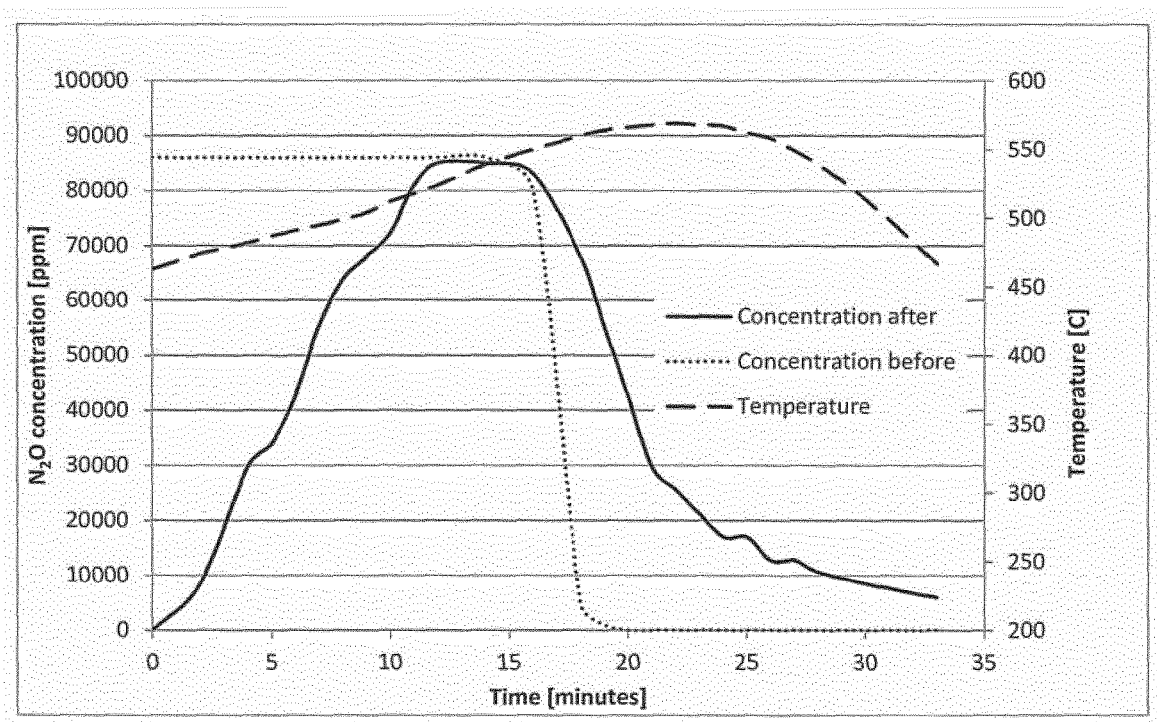
FIG. 5 is a diagram showing how long it takes for the adsorption/desorption means according to the invention to saturate when the flow of nitrous oxide is kept constant at 7 g/min (corresponding to a mass flow of about 85 000 ppm) up to about 16 minutes, where after this flow is zero and how long it takes for the adsorption/desorption means to be flushed.

FIG. 5 shows an experiment in which the flow of nitrous oxide was kept constant at 7 g/min up to about 16 minutes. This corresponds to a concentration of about 85 000 ppm. After this, the flow of nitrous oxide is zero. Shown by dotted line.

Throughout the process, the electric heater is turned off, i.e. no heat was added.

In the same figure is shows how long it takes for the activated carbon means to saturate and how long it takes for the same to be flushed when concentration of nitrous oxide is zero. Shown by continuous black line.

As shown, it takes about 18-19 minutes until the concentration of nitrous oxide is down to about 5 000 ppm after the activated carbon means has been saturated and the incoming gas to the activated carbon means contains no nitrous oxide.

For technical reasons the resolution of the measuring was about 3 000-2 000 ppm. For that reason, the curve does not evolve smoothly but more stepwise. In reality, the concentration of nitrous oxide from the activated carbon means reduces "smoother", i.e. more curve like.

The invention claimed is:

1. An apparatus for catalytic decomposition of nitrous oxide in a gas stream derived from exhalation air from a patient, said apparatus comprises:
   a) an inlet arrangement with a gas inlet for the exhalation air,
   b) an outlet arrangement with a gas outlet for an outlet gas, and between these arrangements
   c) a through-flow decomposition chamber containing a catalyst material promoting the decomposition of nitrous oxide to $N_2$ and $O_2$,
   wherein the apparatus further comprises a control unit for controlling and monitoring the temperature and flow of the gas stream in the through-flow decomposition chamber and, in the flow direction of the gas stream from gas inlet and before the through-flow decomposition chamber, a fan, a flow meter, a heat exchanger arranged to transfer heat from the outlet gas to the exhalation air, and an electrical heater, and
   wherein the inlet arrangement comprises at least one nitrous oxide adsorption/desorption means comprising a container filled with activated carbon or zeolite for adsorbing/desorbing nitrous oxide to level out variations in the concentration of nitrous oxide fed to the decomposition chamber.

2. The apparatus according to claim 1, wherein in case the container is filled with activated carbon, the activated carbon is of the type bituminous coal based or coconut, having a surface area of about 500 to 2000 m$^2$/g.

3. The apparatus according to claim 1, wherein said at least one nitrous oxide adsorption/desorption means is heated to increase the desorption rate of the nitrous oxide, if necessary.

4. The apparatus according to claim 1, wherein the electrical heater is arranged to heat only an incoming gas during the start-up phase of the apparatus.

5. The apparatus according to claim 1, wherein the apparatus is mobile and adapted to be directly connected to at least one patient.

* * * * *